US007915422B2

(12) United States Patent
Kumar et al.

(10) Patent No.: US 7,915,422 B2
(45) Date of Patent: Mar. 29, 2011

(54) PROCESSES FOR THE PREPARATION OF SUBSTITUTED SULFOXIDES

(75) Inventors: Neela Praveen Kumar, Andhra Pradesh (IN); Mahavir Singh Khanna, Delhi (IN); Mohan Prasad, Haryana (IN); Yatendra Kumar, Haryana (IN)

(73) Assignee: Ranbaxy Laboratories Limited, New Delhi (IN)

( * ) Notice: Subject to any disclaimer, the term of this patent is extended or adjusted under 35 U.S.C. 154(b) by 708 days.

(21) Appl. No.: 11/576,867

(22) PCT Filed: Oct. 4, 2005

(86) PCT No.: PCT/IB2005/002946
§ 371 (c)(1),
(2), (4) Date: Feb. 20, 2008

(87) PCT Pub. No.: WO2006/040635
PCT Pub. Date: Apr. 20, 2006

(65) Prior Publication Data
US 2008/0275245 A1    Nov. 6, 2008

(30) Foreign Application Priority Data

Oct. 11, 2004    (IN) ............... 1957/DEL/2004

(51) Int. Cl.
*C07D 401/12*    (2006.01)
(52) U.S. Cl. .................................................. 546/273.7
(58) Field of Classification Search ................. 546/273.7
See application file for complete search history.

(56) References Cited

U.S. PATENT DOCUMENTS

| 5,386,032 | A | 1/1995 | Brändström | 546/271 |
| 5,948,789 | A | 9/1999 | Larsson et al. | 514/299 |
| 6,166,213 | A | 12/2000 | Anousis et al. | 546/273.7 |
| 6,229,021 | B1 | 5/2001 | Šmahovský et al. | 548/306.1 |
| 6,268,502 | B1 | 7/2001 | Milač et al. | 546/273.7 |
| 6,303,788 | B1 | 10/2001 | Cotton et al. | 546/273.7 |
| 6,603,009 | B2 | 8/2003 | Maimo et al. | 546/273.4 |
| 2003/0171591 | A1 | 9/2003 | Hashimoto et al. | 546/273.7 |

FOREIGN PATENT DOCUMENTS

| WO | WO 99/47514 | 9/1999 |
| WO | WO 03/089408 | 10/2003 |

OTHER PUBLICATIONS

Zhao et al., "Asymmetric Oxidation of Sulfides Mediated by Chiral Titanium Complexes: Mechanistic and Synthetic Aspects", *Tetrahedron*, 43(21):5135-5144 (1987).
Pitchen et al. "An Efficient Asymmetric Oxidaton of Sulfides to Sulfoxides", *Journal of the American Chemical Society*, 106(26):8188-8193 (1984).

*Primary Examiner* — Patricia L Morris

(57) ABSTRACT

The present invention relates to a process for enantioselective synthesis of substituted pyridinylmethyl sulfinyl-benzimidazole of compound of Formula (I). The process includes enantioselective catalytic oxidation of a substituted pyridinylmethyl prochiral sulfide derivative of compound of Formula (II) with an oxidizing agent in the presence of a chiral transition metal complex and a base in the absence of an organic solvent.

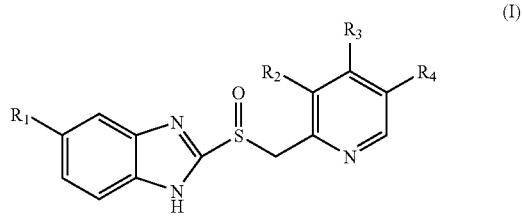

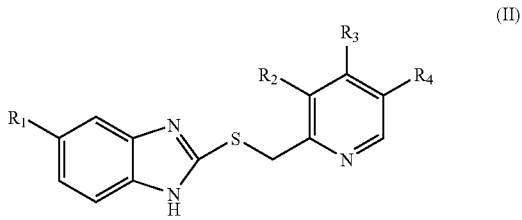

20 Claims, No Drawings

PROCESSES FOR THE PREPARATION OF SUBSTITUTED SULFOXIDES

FIELD OF THE INVENTION

The present invention relates to processes for the enantioselective synthesis of substituted pyridinylmethyl sulfinyl-benzimidazoles of the compound of Formula I,

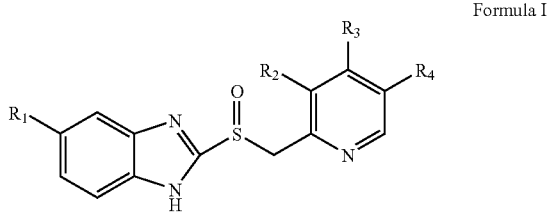

Formula I wherein $R_1$ to $R_4$ represent hydrogen, $C_1$ to $C_4$ represent linear or branched alkyl, $C_1$ to $C_4$ represent linear or branched alkoxy, aryl, aryloxy or their halo or alkoxy substituted analogs. The process includes enantioselective catalytic oxidation of a substituted pyridinylmethyl prochiral sulfide derivative of compound of Formula II,

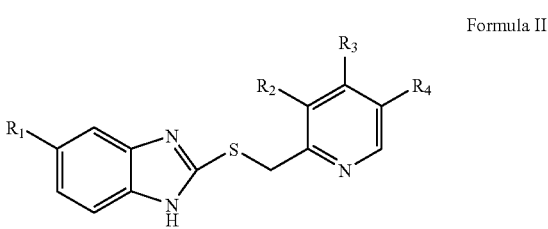

Formula II wherein $R_1$ to $R_4$ are as defined above, in the absence of an organic solvent. The products obtained may thereafter be converted to pharmaceutically acceptable salts thereof by conventional processes.

BACKGROUND OF THE INVENTION

Optically active substituted pyridinylmethyl sulfinyl-benzimidazole enantiomers and their pharmaceutically acceptable salts are proton pump inhibitors, which are useful as antiulcer agents. These compounds include omeprazole, lansoprazole, rabeprazole, pantoprazole, pariprazole and leminoprazole.

There are several patents and patent applications disclosing oxidation of prochiral sulfide. U.S. Pat. No. 6,166,213 describes a process for the preparation of omeprazole by oxidation of pyrmetazole in the presence of meta chloroperoxybenzoic acid. U.S. 2003/0171591 discloses a method of producing benzimidazoles comprising oxidizing sulfide with an excess of oxidizing agent in the presence of a catalyst for asymmetric induction. U.S. Pat. No. 6,229,021 describes a process for the preparation of omeprazole comprising oxidizing its corresponding thioether with peroxyacetic acid in a two-phase water and chlorinated organic solvent medium. U.S. Pat. No. 6,268,502 describes a process for the preparation of omeprazole comprising oxidizing its corresponding thioether with 3-chloroperoxybenzoic acid in ethyl acetate. U.S. Pat. No. 6,603,009 discloses a process for the preparation of omeprazole comprising oxidizing its corresponding thioether with sodium percarbonate and molybdenum salt catalyst. U.S. Pat. No. 5,386,032 claims a process for the preparation of omeprazole comprising oxidizing its corresponding thioether with m-chloroperoxybenzoic acid at specific pH. PCT application WO 99/47514 discloses a method of producing benzimidazole compounds comprising oxidizing its corresponding thioether with perborate salt.

PCT application WO 03/089408 describes an enantioselective catalytic oxidation of sulfide with an oxidizing agent, in an organic solvent, base and in the presence of titanium or vanadium complexed with a monodentate ligand. Toluene is used in Example 1 of WO 03/089408 as an organic solvent. In general, it should be noted that solvents are used in excess and as a liquid that dissolves the solid to make a solution. Thus, if the amount of a purported solvent is too low to dissolve all the reactants and reagents, it is not considered to be a solvent. In this manner, for example, an organic compound can be used either as a solvent if it is provided in excess or only as a base if it is not provided in a quantity sufficient to function as a solvent.

U.S. Pat. No. 5,948,789 describes oxidation of a pro-chiral sulfide with an oxidizing agent and chiral titanium complex in an organic solvent. Each and every reference in the prior art literature of which the inventors are aware discloses the use of organic solvent in the catalytic oxidation.

SUMMARY OF THE INVENTION

In one general aspect there is provided an enantioselective catalytic oxidation process for the preparation of an optically active enantiomer or an enantiomerically enriched form of substituted pyridinylmethyl sulfinyl-benzimidazole of compound of Formula I

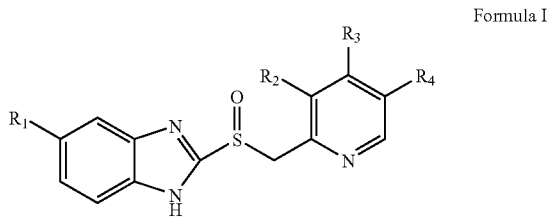

Formula I wherein $R_1$ to $R_4$ represent hydrogen, $C_1$ to $C_4$ represent linear or branched alkyl, $C_1$ to $C_4$ represent linear or branched alkoxy, aryl, aryloxy or its pharmaceutically acceptable salts, the process comprising oxidizing a pro-chiral sulfide of Formula II,

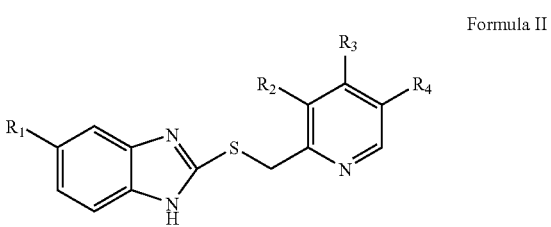

Formula II wherein $R_1$ to $R_4$ are the same as defined above, in the presence of a chiral transition metal complex and a base in the absence of an organic solvent.

Embodiments of the process may include one or more of the following features. For example, the prochiral sulfide may be obtained as a solution directly from a reaction mixture in which it is formed.

The reaction may be carried out in the presence of an oxidizing agent. The oxidizing agent may be selected from the group comprising hydrogen peroxide, alkyl hydro peroxide and aryl alkyl hydro peroxide. The aryl alkyl hydro peroxide may be cumene hydro peroxide.

The transition metal may be selected from the group comprising titanium, zirconium and vanadium. The transition metal complex may be prepared from a transition metal alkoxide and a chiral ligand. The transition metal alkoxide may be titanium isopropoxide.

The chiral ligand may be a chiral branched or unbranched alkyl diol or an aromatic diol. The chiral diol may be a chiral ester of tartaric acid. The chiral ester may be (+)-diethyl L-tartrate.

The metal complex may be added to the reaction mixture containing prochiral sulfide. The reaction mixture containing prochiral sulfide may be added to the metal complex.

The base may be an organic or inorganic base. The organic base may be selected from the group comprising trimethylamine, triethylamine, tributylamine, triisopropylamine, diisopropylethylamine, pyridine, morpholine, DBU (1,8-diazabicyclo-[5.4.0]-undec-7-ene), DBN (1,5-diazabicyclo-[4.3.0]-non-5-ene), 4-dimethylamino pyridine and mixtures thereof. The inorganic base may be selected from the group comprising alkali metal carbonate, alkali metal bicarbonate and alkali metal hydroxide.

The enantioselective catalytic oxidation may be carried out at a temperature in the range of about 20-40° C. The enantioselective catalytic oxidation may be carried out for a period of about 1-8 hours.

The obtained sulfoxide may be converted into a pharmaceutically acceptable salt selected from optically active alkali and alkaline earth metal salts. The optically active alkali or alkaline earth metal salt may be prepared by treating with an alkali or alkaline earth metal source comprising bicarbonates, carbonates, hydrides, hydroxides, halides, sulphates and oxides.

The obtained products may thereafter be converted to their pharmaceutically acceptable salts by known, conventional processes.

Compounds prepared by the enantioselective catalytic oxidation process of the present invention are optically active enantiomer or enantiomerically enriched forms of substituted pyridinylmethyl-sulfinyl-benzimidazole of the compounds of Formula I.

More specifically, the process of the present invention provides an enantioselective catalytic oxidation process for the preparation of optically active or enantiomerically enriched sulfoxides of omeprazole, pantoprazole, rabeprazole and lansoprazole, which are proton pump inhibitors useful in the treatment of ulcers.

The process of the present invention further provides a process for the preparation of alkali and/or alkaline earth metal salts of an optically active enantiomer or an enantiomerically enriched form of substituted pyridinylmethyl-sulfinyl-benzimidazole, compound of Formula I, prepared by enantioselective catalytic oxidation of a substituted pyridinylmethyl prochiral sulfide derivative of compound of Formula II.

The details of one or more embodiments of the inventions are set forth in the description below. Other features, objects and advantages of the inventions will be apparent from the description and claims.

DETAILED DESCRIPTION OF THE INVENTION

The prochiral sulfide may be prepared by any of the various methods known in the art. The prochiral sulfide may also be obtained as a solution, for example from a reaction mixture resulting directly from a reaction in which it is formed.

Examples of oxidizing agents used in the inventive process include one or more of hydrogen peroxide, alkylhydroperoxides, arylalkyl hydroperoxide and mixtures thereof. Example of alkylhydroperoxide includes tertiary butyl hydroperoxide. An example of arylalkyl hydroperoxide includes cumene hydroperoxide. The oxidizing agent may be added slowly, for example, over a period of thirty minutes to ninety minutes.

Catalytic oxidation may be carried out in the presence of a transition metal catalyst selected from titanium, vanadium and zirconium compounds. The catalyst may be used in the form of complex. A complex suitable for catalyzing the process of the invention may be prepared from a chiral ligand and transition metal compounds.

Examples of transition metal compounds include their alkoxide or acetate form, such as titanium (IV) isopropoxide or vanadium acetate. The titanium complex also may be prepared by reacting titanium tetrachloride with a chiral ligand in the presence of a base. The metal complex may be added slowly to a reaction mixture containing the prochiral sulfide or the prochiral sulfide with an oxidizing agent, and optionally the base may be added to the complex.

The chiral ligand used in the preparation of the metal complex may be a chiral alcohol such as a chiral diol. The diol may be a branched or unbranched alkyl diol, or an aromatic diol. Preferred chiral diols are esters of tartaric acid and, in particular, (+)-diethyl L-tartrate. It has been observed that use of (+)-diethyl L-tartrate gives the (S)-isomer of sulfoxide whereas (−)-diethyl D-tartrate gives the R-isomer of the corresponding sulfoxide.

According to the process of the present invention the enantioselective catalytic oxidation process may be carried out in the presence of a base. The base may be an organic or inorganic base. Examples of organic base include trimethylamine, triethylamine, tributylamine, triisopropylamine, diisopropylethylamine, pyridine, morpholine, DBU (1,8-diazabicyclo-[5.4.0]-undec-7-ene), DBN (1,5-diazabicyclo-[4.3.0]-non-5-ene), 4-dimethylamino pyridine and mixtures thereof. Examples of inorganic bases include alkali metal carbonate, bicarbonate, hydroxide and mixtures thereof. Examples of alkali metal carbonates include lithium carbonate, sodium carbonate and potassium carbonate. Examples of alkali metal bicarbonates include sodium bicarbonate and potassium bicarbonate. Examples of alkali metal hydroxides include sodium hydroxide and potassium hydroxide. The amount of base is not critical and may be adjusted with respect to reaction mixture.

According to the process of the present invention the enantioselective catalytic oxidation reaction may be carried out at a temperature in the range of about 20-40° C., in particular in the range of about 25-30° C. for a period of 1-8 hours, and more particularly for about 2-6 hours.

The process of the present invention includes the preparing an optically active alkali and/or alkaline earth metal salt of substituted pyridinylmethyl-sulphinyl-benzimidazole by treating the optically active substituted pyridinylmethyl-sulphinyl-benzimidazole compound of Formula I, obtained by enantioselective catalytic oxidation of substituted pyridinylmethyl prochiral sulfide derivative of benzimidazole, compound of Formula II, with an alkali and/or alkaline earth metal source. The alkali or alkaline earth metal source may be selected from $Na^+$, $Li^+$, $Mg^{+2}$, $Ca^{+2}$ and $Ba^{+2}$ salts such as bicarbonates, carbonates, hydrides, hydroxides, halides, sulphates, and oxides. In particular, sodium hydroxide, potassium hydroxide, barium hydroxide, lithium hydroxide, magnesium hydroxide, calcium halide, magnesium halide and barium halide may be used.

The process of the present invention further includes the optional steps of isolating the alkali or alkaline earth metal salts of the optically active substituted pyridinylmethyl-sulfinyl-benzimidazole compound of Formula I by solvent evaporation with or without vacuum, addition of the same or different solvent and filtering the product, and drying followed by crystallization, as required.

The products described above can be further processed if desired. Alkali or alkaline earth metal salts of benzimidazole compounds may be converted to another alkali or alkaline earth metal salts of these compounds. For example, esomeprazole barium can be converted into esomeprazole magnesium. The process may be as follows:
 a) conversion of esomeprazole barium into esomeprazole base by adjusting the pH (6.8-7.0) with dilute hydrochloric acid and its extraction with dichloromethane;
 b) conversion of esomeprazole base into esomeprazole magnesium by adding a catalytic amount of diisopropyl ethylamine and methanolic potassium hydroxide followed by magnesium sulphate; and
 c) isolation of esomeprazole magnesium using acetone as a solvent.

The products described and/or disclosed above, or after conversion into esomeprazole magnesium, may be formulated into a dosage form, e.g., tablet, capsule, etc., by combining with one or more pharmaceutically acceptable excipients using known techniques. The resulting dosage form may include a suitable amount of the active ingredient. For example, the resulting dosage form may contain between 5 and 50 mg of esomeprazole magnesium. Further, the dosage form may be conventional release or extended release. The dosage forms may be administered as proton pump inhibitors useful for treating ulcers. The dosage forms may further contain one or more additional active ingredients or be marketed in the form of a kit with additional active ingredients suitable for administration with esomeprazole magnesium.

The following embodiments are provided as examples to illustrate the processes of the invention. These examples are not intended to limit the scope of the present invention and it is expected that variants of these examples will be evident to persons of ordinary skill in the art.

EXAMPLES

Example 1

Preparation of the potassium salt of 5-methoxy-2-[(S)-(4-methoxy-3,5-dimethyl-2-pyridinylmethyl) sulphinyl]-1H-benzimidazole (esomeprazole potassium)

A solution of titanium isopropoxide (2.08 g, 0.0073 mol) and L (+) Diethyl tartrate (3.12 g, 0.015 mol) was heated to 45 to 50° C. and stirred for 90 minutes. The above mass was cooled to 25 to 30° C. and a mixture of omeprazole sulfide (10 g, 0.03 mol), cumene hydroperoxide (70% solution, 8.6 g, 0.0315 mol), L (+) diethyl tartrate (4 g, 0.019 mol) and diisopropyl ethylamine (3.92 g, 0.03 mol) was added to this complex. The reaction mixture was stirred at 25 to 35° C. for eight hours. Toluene (100 ml) and water (100 ml) was then added to the reaction mixture and stirred for 10 minutes. The toluene layer was separated and methanolic potassium hydroxide solution (4.26 g in 30 ml methanol) was added to the toluene layer. The mixture was stirred for 15 to 16 hours at 25 to 35° C. The product was filtered under nitrogen atmosphere and washed with a mixture of toluene and methanol followed by hexane. The product was dried under reduced pressure at 50 to 55° C.

| | |
|---|---|
| Yield = | 6.5 g |
| Enantiomeric excess = | 99% |
| Sulfone content = | 2.67%, |
| HPLC Purity = | 96.83% |

Example 2

Preparation of the potassium salt of 5-methoxy-2-[(R)-(4-methoxy-3,5-dimethyl-2-pyridinylmethyl) sulphinyl]-1H-benzimidazole (R-omeprazole potassium)

A solution of titanium isopropoxide (2.08 g, 0.0073 mol) and D (−) Diethyl tartrate (3.12 g, 0.015 mol) was heated to 45 to 50° C. and stirred for 90 minutes. The above mass was cooled to 25 to 30° C. and a mixture of omeprazole sulfide (10 g, 0.03 mol), cumene hydroperoxide (70% solution, 8.6 g, 0.0315 mol), D (−) diethyl tartrate (4 g, 0.019 mol) and diisopropyl ethylamine (3.92 g, 0.03 mol) was added to this complex. The reaction mixture was stirred at 25 to 35° C. for eight hours. Toluene (100 ml) and water (100 ml) was then added to the reaction mixture and stirred for 10 minutes. The toluene layer was separated and a methanolic potassium hydroxide solution (4.26 g in 30 ml methanol) was added to the toluene layer. The mixture was stirred for 15 to 16 hours at 25 to 35° C. The product was filtered under nitrogen atmosphere and washed with a mixture of toluene and methanol followed by hexane. The product was dried under reduced pressure at 50 to 55° C.

| | |
|---|---|
| Yield = | 6.5 g |
| Enantiomeric excess = | 98% |
| HPLC Purity = | 98.0% |

Example 3

Preparation of the barium salt of 5-methoxy-2-[(S)-(4-methoxy-3,5-dimethyl-2-pyridinylmethyl)sulphinyl]-1H-benzimidazole (esomeprazole barium)

A solution of titanium isopropoxide (5.2 g 0.018 mol) and L (+) Diethyl tartrate (7.8 g, 0.037 mol) was heated to 45 to 50° C. and the reaction mixture stirred for 90 minutes. The solution was cooled to 25 to 30° C. and a mixture of omeprazole sulfide (25 g, 0.0759 mol), cumene hydro peroxide (70% solution, 17.32 g, 0.0797 mol), L (+) diethyl tartrate (10 g, 0.0485 mol) and diisopropyl ethylamine (9.8 g, 0.0797 mol) was added to the above complex. The reaction mixture was stirred at 25 to 35° C. for eight hours. Toluene (250 ml) and water (250 ml) was then added to the reaction mixture and the reaction mixture was stirred for 10 minutes. The toluene layer was separated and a methanolic barium hydroxide solution (14.36 g in 200 ml methanol) was added to the toluene layer. The solvent was evaporated under reduced pressure and methanol (250 ml) was added to the residue. The mixture was stirred for 15 to 16 hours at 25 to 35° C. The product was filtered and washed with methanol. The product was dried under reduced pressure at 50 to 55° C.

| Yield = | 11 g |
|---|---|
| Enantiomeric excess = | 99% |
| HPLC Purity = | 98% |

Example 4

Preparation of the potassium salt of 5-methoxy-2-[(S)-(4-methoxy-3,5-dimethyl-2-pyridinylmethyl)sulphinyl]-1H-benzimidazole (esomeprazole potassium)

A solution of titanium isopropoxide (5.2 g 0.018 mol) and L (+) Diethyl tartrate (17.8 g, 0.086 mol) was heated to 45 to 50° C. and the reaction mixture stirred for 90 minutes. The solution was cooled to 25 to 30° C. and a mixture of omeprazole sulfide (25 g, 0.0759 mol) and diisopropyl ethylamine (9.8 g, 0.0797 mol) was added to the above complex. Cumene hydro peroxide (70% solution, 17.32 g, 0.0797 mol) was then added slowly over a period of one hour. The reaction mixture was stirred at 25 to 35° C. for 3 hours. Toluene (250 ml) and water (250 ml) was then added to the reaction mixture and the reaction mixture stirred for 10 minutes. The toluene layer was separated and methanolic potassium hydroxide solution (10.32 g in 75 ml methanol) was added to the toluene layer. The mixture was stirred for 15 to 16 hours at 25 to 35° C. The product was filtered under nitrogen atmosphere and washed with a mixture of toluene and methanol followed by hexane. The product was dried under reduced pressure at 50 to 55° C.

| Yield = | 17.3 g |
|---|---|
| Enantiomeric excess = | 90% |
| Sulfone content = | 2.39%, |
| HPLC Purity = | 97% |

Example 5

Preparation of the potassium salt of 5-methoxy-2-[(S)-(4-methoxy-3,5-dimethyl-2-pyridinylmethyl)sulphinyl]-1H-benzimidazole (esomeprazole potassium)

A solution of titanium isopropoxide (5.2 g, 0.018 mol) and L (+) Diethyl tartrate (7.8 g, 0.037 mol) was heated to 45 to 50° C. and the reaction mixture stirred for 90 minutes. The solution was cooled to 25 to 30° C. A mixture of omeprazole sulfide (25 g, 0.0759 mol), cumene hydroperoxide (70% solution, 17.32 g, 0.0797 mol), L (+) diethyl tartrate (8.5 g, 0.0412 mol) and diisopropyl ethylamine (9.8 g, 0.0797 mol) was prepared separately. The above-prepared complex was added slowly to this slurry of omeprazole sulfide at 25-30° C. The reaction mixture was stirred at 25 to 35° C. for 3 hours. Toluene (250 ml) and water (250 ml) was then added to the reaction mixture and the reaction mixture was stirred for 10 minutes. The toluene layer was separated and methanolic potassium hydroxide solution (10.32 g in 75 ml methanol) was added to the toluene layer. The mixture was stirred for 15 to 16 hours at 25 to 35° C. The product was filtered under nitrogen atmosphere and washed with a mixture of toluene and methanol followed by hexane. The product was dried under reduced pressure at 50 to 55° C.

| Yield = | 17.0 g |
|---|---|
| Enantiomeric excess = | 99% |
| Sulfone content = | 2.36%, |
| HPLC Purity = | 97.41% |

Example 6

Preparation of the potassium salt of 5-methoxy-2-[(S)-(4-methoxy-3,5-dimethyl-2-pyridinylmethyl)sulphinyl]-1H-benzimidazole (esomeprazole potassium)

A solution of titanium isopropoxide (2.08 g, 0.0073 mol) and L (+) Diethyl tartrate (3.12 g, 0.015 mol) was heated to 45 to 50° C. and the reaction mixture stirred for 90 minutes. The above mass was cooled to 25 to 30° C. and a mixture of omeprazole sulfide (10 g, 0.03 mol), cumene hydro peroxide (83% solution, 8.6 g, 0.0355 mol), L (+) diethyl tartrate (4 g, 0.019 mol) and diisopropyl ethylamine (3.92 g, 0.03 mol) was added to this complex. The reaction mixture was stirred at 25 to 35° C. for eight hours. Toluene (100 ml) and water (100 ml) was then added to the reaction mixture and stirred for 10 minutes. The toluene layer was separated and methanolic potassium hydroxide solution (4.26 g in 30 ml methanol) was added to the toluene layer. The mixture was stirred for 15 to 16 hours at 25 to 35° C. The product was filtered under nitrogen atmosphere and washed with mixture of toluene and methanol followed by hexane. The product was dried under reduced pressure at 50 to 55° C.

| Yield = | 6.5 g |
|---|---|
| Enantiomeric excess = | 99% |
| Sulfone content = | 2.67%, |
| HPLC Purity = | 96.83% |

Example 7

Preparation of the barium salt of 5-methoxy-2-[(S)-(4-methoxy-3,5-dimethyl-2-pyridinylmethyl)sulphinyl]-1H-benzimidazole (esomeprazole barium)

Titanium isopropoxide (1.96 kg, 6.89 mol) and L (+) Diethyl tartrate (2.52 kg, 12.22 mol) were heated to 50 to 55° C. and the reaction mixture stirred for 90 minutes. The solution was cooled to 10 to 15° C., the complex so prepared was added to a suspension containing cumene hydro peroxide (82% solution, 5.04 kg, 27.15 mol), and diisopropyl ethylamine (2.744 kg, 21.23 mol) and omeprazole sulfide (7.0 kg, 21.25 mol) at 10 to 15° C. over a period of 5-10 minutes. The reaction mixture was stirred at 10 to 35° C. for 3-4 hours. Water (70 L) was then added to the reaction mixture under stirring followed by toluene (70 L) and the reaction mixture was stirred for 15-20 minutes. The toluene layer was separated and added to the solution containing potassium hydroxide (2.38 kg, 42.5 mol) and water (70 L) and stirred for 30 minutes. The aqueous layer was separated and dichloromethane (35 L) was added. The solution was acidified to pH 6.0-7.0 with dilute hydrochloric acid. The organic layer was then separated and solvent was recovered under reduced pressure in the presence of diisopropyl ethyl amine (70 ml). Methanol (14 L) was added to the residue and filtered to remove any suspended solid. The filtrate so obtained was added to the methanolic barium hydroxide solution (39.2 kg in 56 L methanol) and stirred for 10-12 hours at 25 to 35° C. The product was filtered and washed with methanol. The product was dried under reduced pressure at 50 to 55° C.

| Yield = | 2.70 kg |
|---|---|
| Enantiomeric excess = | 99% |
| HPLC Purity = | 98% |

Example 8

Preparation of the barium salt of 5-methoxy-2-[(S)-(4-methoxy-3,5-dimethyl-2-pyridinylmethyl)sulphinyl]-1H-benzimidazole (esomeprazole barium)

Titanium isopropoxide (14 g, 0.049 mol) and L (+) Diethyl tartrate (36 g, 0.175 mol) were heated to 50 to 55° C. and the reaction mixture stirred for 90 minutes. The solution was cooled to 10 to 15° C. and the complex so prepared was added to a suspension containing cumene hydro peroxide (82% solution, 72 g, 0.387 mol), diisopropyl ethylamine (39.2 g, 0.303 mol) and omeprazole sulfide (100 g, 0.303 mol) at 10 to 15° C. over a period of 5-10 minutes. The reaction mixture was stirred at 10 to 35° C. for 3-4 hours. Water (1000 ml) was then added to the reaction mixture under stirring followed by toluene (1000 ml) and the reaction mixture was stirred for 15-20 minutes. The toluene layer was separated and added in to the solution containing potassium hydroxide (34 g, 0.607 mol) and water (1000 ml) and stirred for 30 minutes. The aqueous layer was separated and dichloromethane (500 ml) was added. The resulting solution was acidified to pH 6.0-7.0 with dilute hydrochloric acid. The organic layer was then separated and solvent recovered under reduced pressure in the presence of diisopropyl ethyl amine (1.0 g). Methanol (200 ml) was added to the residue and filtered to remove any suspended solid. The filtrate so obtained was added to a methanolic barium hydroxide solution (56 g in 400 ml methanol) and stirred for 10-12 hours at 25 to 35° C. The product was filtered and washed with methanol. The product was dried under reduced pressure at 50 to 55° C.

| Yield = | 37 g |
|---|---|
| Enantiomeric excess = | 99% |
| HPLC Purity = | 98% |

Example 9

Preparation of the magnesium salt of 5-methoxy-2-[(S)-(4-methoxy-3,5-dimethyl-2-pyridinylmethyl)sulphinyl]-1H-benzimidazole (esomeprazole magnesium)

A mixture of DM water (3500 ml), esomeprazole barium (350 g) and dichloromethane (2.8 L ml) was cooled to 15 to 16° C. The pH was adjusted to 7.0 to 8.0 with 3 N hydrochloric acid at 15 to 17° C. and the mixture stirred at 15 to 20° C. The organic layer was separated and washed with DM water (175 ml). Diisopropylamine was added to the organic layer. The solvent was recovered under reduced pressure at 30-35° C. The residue was cooled to 25-30° C. Methanol (2450 ml) and activated carbon (17.5 g) were then added at 25-30° C. The temperature was raised to 30-35° C. and the mixture was stirred for 30 minutes at this temperature. The reaction mixture was filtered through hyflo bed and the hyflo bed washed with methanol (700 ml). A potassium hydroxide solution (56 g dissolved in 262 ml methanol) was then added to the above mixture at 10-25° C. Magnesium sulfate (129.5 g) was added at 25-30° C. and the temperature was raised to 34-37° C. The mixture was stirred for 90 minutes at 34-37° C. and inorganic salts were filtered through the hyflo bed. The hyflo bed was washed with hot methanol (2000 ml, preheated to 40° C.). Methanol (~95%) was recovered under reduced pressure below 40-45° C. and acetone (2000 ml) was added to the residue. The residue was cooled to 30-35° C. and stirred for 1 hour. Again the residue was cooled to 20-25° C. and stirred for 4-5 hours. The solid was filtered and washed with acetone (1400 ml, precooled to 5-10° C.). The wet material was dried under reduced pressure for 4-5 hours at 40-45° C.

| Yield = | 224 g (w/w) |
|---|---|
| HPLC Purity = | 99.6% |
| Chiral purity by HPLC = | 100% |

While several particular forms of the inventions have been described, it will be apparent that various modifications and combinations of the inventions detailed in the text can be made without departing from the spirit and scope of the inventions. Accordingly, it is not intended that the inventions be limited, except as by the appended claims.

We claim:
1. An enantioselective catalytic oxidation process for the preparation of an optically active enantiomer or an enantiomerically enriched form of substituted pyridinylmethyl sulfinyl-benzimidazole of compound of Formula I

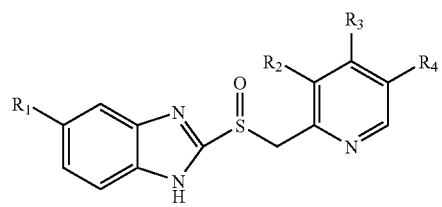

Formula I wherein $R_1$ to $R_4$ represent hydrogen, $C_1$ to $C_4$ represent linear or branched alkyl, $C_1$ to $C_4$ represent linear or branched alkoxy, aryl, aryloxy or its pharmaceutically acceptable salts, the process comprising oxidizing a prochiral sulfide of Formula II,

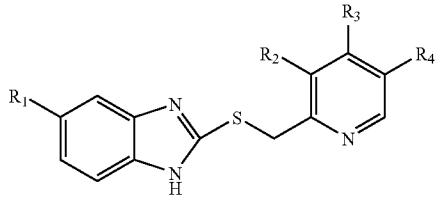

Formula II wherein $R_1$ to $R_4$ are the same as defined above, in the presence of a chiral transition metal complex and a base in the absence of an organic solvent.

2. The process according to claim 1, wherein the prochiral sulfide is obtained as a solution directly from a reaction mixture in which it is formed.

3. The process according to claim 1, wherein the reaction is carried out in the presence of an oxidizing agent.

4. The process according to claim 3, wherein the oxidizing agent is selected from the group comprising hydrogen peroxide, alkyl hydro peroxide and aryl alkyl hydro peroxide.

5. The process according to claim 4, wherein the aryl alkyl hydro peroxide comprises cumene hydro peroxide.

6. The process according to claim 1, wherein the transition metal is selected from the group comprising titanium, zirconium and vanadium.

7. The process according to claim 1, wherein the transition metal complex is prepared from a transition metal alkoxide and a chiral ligand.

8. The process according to claim 7, wherein the transition metal alkoxide comprises titanium isopropoxide.

9. The process according to claim 1, wherein the chiral ligand comprises a chiral branched or unbranched alkyl diol or an aromatic diol.

10. The process according to claim 9, wherein the chiral diol is a chiral ester of tartaric acid.

11. The process according to claim 10, wherein the chiral ester comprises (+)-diethyl L-tartrate.

12. The process according to claim 1, wherein the metal complex is added to the reaction mixture containing prochiral sulfide.

13. The process according to claim 1, wherein the reaction mixture containing prochiral sulfide is added to the metal complex.

14. The process according to claim 1, wherein the base is an organic or inorganic base.

15. The process according to claim 14, wherein the organic base is selected from the group comprising trimethylamine, triethylamine, tributylamine, triisopropylamine, diisopropylethylamine, pyridine, morpholine, DBU (1,8-diazabicyclo-[5.4.0]-undec-7-ene), DBN (1,5-diazabicyclo-[4.3.0]-non-5-ene), 4-dimethylamino pyridine and mixtures thereof.

16. The process according to claim 14, wherein inorganic base is selected from the group comprising alkali metal carbonate, alkali metal bicarbonate and alkali metal hydroxide.

17. The process according to claim 1, wherein the enantioselective catalytic oxidation is carried out at a temperature in the range of about 20-40° C.

18. The process according to claim 1, wherein the enantioselective catalytic oxidation is carried out for a period of about 1-8 hours.

19. The process according to claim 1, wherein the obtained sulfoxide is converted into a pharmaceutically acceptable salt selected from optically active alkali and alkaline earth metal salts.

20. The process according to claim 19, wherein the optically active alkali or alkaline earth metal salt is prepared by treating with an alkali or alkaline earth metal source comprising bicarbonates, carbonates, hydrides, hydroxides, halides, sulphates and oxides.

* * * * *